United States Patent [19]

Nielsen et al.

[11] Patent Number: 4,990,541

[45] Date of Patent: Feb. 5, 1991

[54] WATER ABSORBENT LATEX POLYMER FOAMS

[75] Inventors: Steven F. Nielsen, Charlotte, N.C.; Dai W. Kim, Chatham, N.J.

[73] Assignee: Hoechst Celanese Corp., Somerville, N.J.

[21] Appl. No.: 434,376

[22] Filed: Nov. 9, 1989

[51] Int. Cl.$^5$ .................................................. C08J 9/28
[52] U.S. Cl. ..................................... 521/70; 521/84.1; 521/139; 521/140; 521/134
[58] Field of Search ............................................ 521/70

[56] References Cited

U.S. PATENT DOCUMENTS

| | | | |
|---|---|---|---|
| 3,959,197 | 5/1976 | Salyer et al. | 521/59 X |
| 4,000,028 | 12/1976 | Hoey | 521/69 X |
| 4,076,663 | 2/1978 | Masuda et al. | 525/54.31 |
| 4,497,930 | 2/1985 | Yamasaki et al. | 525/54.24 X |
| 4,910,250 | 3/1990 | Saotome | 524/556 |

*Primary Examiner*—Earl Nielsen
*Assistant Examiner*—John Cooney
*Attorney, Agent, or Firm*—Lynch, Cox, Gilman & Mahan

[57] ABSTRACT

A water absorbent latex polymer foam produced by the process of combining a foamed latex polymer product with a water absorbent polymer and drying that blend to form a foamable latex polymer containing a water absorbent polymer is disclosed in this invention. The latex foams produced by this process are of great use, for example, within diapers, sanitary napkins, packaging materials, and the like. In particular, the use of water absorbent polymers with particle size less than about 30 microns has been shown to produce particularly effective absorbent latex foams.

12 Claims, No Drawings

WATER ABSORBENT LATEX POLYMER FOAMS

BACKGROUND OF THE INVENTION

1. Field of Invention

This invention concerns water absorbent polymer articles and a process for their production. More particularly, the invention discloses a starch or cellulose-based water absorbent polymer combined with a foamable latex polymer to form a latex foam polymer containing a water absorbent polymer within its structure.

2. Prior Art

Recently there has been interest in producing absorbent materials particularly for use in products such as sanitary napkins, diapers, disposable dust cloths, etc. Some of the prior art materials used to form these products have been non-woven fabrics, papers, pulps, spongy urethane resins, natural sponges and the like. However, these materials exhibit relatively low water absorbency, thus failing to satisfy the need for a low volume, highly water absorbent material.

Substitutes for these materials such as cross-linked polyethylene oxides, cross-linked polyvinyl alcohols and hydrolyzed products of starch-polyacrylonitrile-grafted polymers have recently appeared on the market. While these products do show increased water absorbency, they also suffer from significant disadvantages in that their water absorbency is still not sufficiently high to justify their costs and difficulties of production. In addition, some of these materials create disposal problems because they are not biologically degradable.

Japanese Patent Application Kokai, No. 57-92,032 (1982) discloses a polyurethane foam that contains a useful water absorbent polymer wherein the size of the water absorbent resin is in the range from about 200 to 400 microns. This Kokai fails to disclose the combination of a water absorbent polymer with a latex foam.

U.S. Pat. No. 4,725,428 discloses a process for making a crosslinked, super absorbent polyurethane foam which contains a plurality of polycarbonyl moieties convalently attached to the polyurethane through at least one urethane, thiourethane or urea linkage. See also U.S. Pat. No. 4,725,629. However, neither of these patents discloses the combination of a water absorbent polymer with a latex foam.

A biodegradable, highly water absorbent polymer is disclosed in U.S. Pat. No. 4,076,663. While the resins of this patent do show increased water absorbency, their use has been limited to mixing them with sanitary napkins, diapers and other such products wherein the resins are used in their particulate or powder form. Thus, this process fails to disclose the use of this water absorbent resin within a confined structure or for use with other polymers within a latex foamed structure.

U.S. Pat. Nos. 4,454,268, 4,337,181 and 4,133,784 disclose various types of films partially comprised of water absorbent polymers. While these patents disclose starch-based, water absorbent polymers prepared from a combination of starch and ethylene acrylic acid copolymers, they fail to disclose the water absorbent polymer disclosed herein or the mixture of a water absorbent polymer with a conventional latex foamable polymer to form a latex foam which exhibits high water absorbency.

U.S. Pat. No. 3,669,103 discloses water swellable, water insoluble polymeric sorbents for the absorption of aqueous fluids wherein said polymeric sorbents are lightly cross-linked polymers. This patent discloses the use of a polyurethane foam as a support for the polymeric absorbent. However, it fails to disclose the use of a water absorbent polymer in general, the water absorbent polymer disclosed herein, or a latex foam support.

Latex materials, particularly latex foams have been well known for many years. The largest single use of latex today is in foam rubber. Latex foams are frequently used in mattresses, pillows, seat cushions, carpet backing and textile foam laminates. Latex foams also find use in providing cushioning in many types of fabrics such as athletic clothing.

There are numerous processes for the production of latex foams, because of their wide range of utility. See for example, U.S. Pat. Nos. 3,650,995, 4,205,103, and 4,174,415. While numerous latex foam patents exist, none discloses the use of a latex foam containing within its structure a cellulose based water absorbent polymer or a process for production of such a material.

Accordingly, it is an object of this invention to prepare latex foams containing within their structure water absorbent polymers.

It is a further object of this invention to disclose water absorbent latex foams which contain water absorbent polymers within their structure which are useful for the absorbance of fluids while retaining their shape.

It is a still further object of this invention to disclose a process for preparing latex foams containing water absorbent polymers which are secured to a backing to form a water absorbent latex foam laminate.

These and other objects, as well as the scope, nature, and utilization of this invention, will be apparent from the following detail description.

SUMMARY OF THE INVENTION

In accordance with the present invention there is provided a water absorbent polymer latex foam which is produced by the following steps:

a. preparing a foamable latex polymer material;
b. foaming said latex polymer material;
c. blending a water absorbent polymer with the latex foam material; and
d. drying the latex foam material containing the water absorbent polymer within its structure to form a water absorbent latex polymer foam.

The products produced by this process can be highly useful in those areas where high water absorbance is critical, such as for use with diapers, sanitary napkins and the like, packaging material for products which must avoid exposure to water and other products where high water absorbance of a foamed material is important. In addition, this product can be combined with a porous cover sheet to permit the water absorbing latex foam to draw fluid through the porous cover sheet to form water absorbent materials for use in food packaging etc. In addition, this water absorbent latex material can be used with athletic garments such as foot wear, athletic gloves, etc. This product not only absorbs moisture, but when backed with a liquid impermeable product, keeps the moisture away from the skin surface of the individual using the product.

DETAILED DESCRIPTION OF INVENTION

The water absorbent polymers used in the instant invention are solid, water insoluble but water swellable polymers which are capable of absorbing many times their own weight of water or aqueous solutions. These products are polymers of water soluble acrylic or vinyl monomers which are slightly crosslinked with a polyfunctional reactant. Such crosslinked polymers include polyvinylpyrrolidone, sulfonated polystyrene, polysulfoethyl acrylate, poly(2-hydroxyethylacrylate), polyacrylamide, polyacrylic acid, partial and complete alkali metal salts of polyacrylic acid, and the like. Also included are starch modified polyacrylic acids and hydrolyzed polyacrylonitrile and their alkali metal salts.

Useful water absorbing polymers can be made by polymerizing acrylic acid and starch in an aqueous medium using a polyfunctional monomer, e.g., N,N-alkylene-bis-acrylamide, as the crosslinking agent. This process is described in U.S. Pat. No. 4,076,663, which is incorporated by reference. Water absorbing polymers can also be made as described in U.S. Pat. No. 4,340,706, incorporated by reference, by the inverse polymerization of acrylic acid followed by crosslinking with a polyfunctional component, e.g., epichlorohydrin. Other water absorbing polymers and processes for their manufacture are disclosed, for example, in U.S. Pat. Nos. 4,654,039; 3,669,103 and 3,670,731. All of the aforesaid patents are hereby incorporated by reference.

The water absorbing polymers particularly useful in this invention are those described in U.S. Pat. No. 4,076,663. These water absorbing polymers have a particle size of from about 0.5 micron to about 450 microns and are capable of absorbing at least about 15 times their weight of an aqueous fluid. In a preferred embodiment superior absorption capabilities exist where the water absorbing polymer particles are less than about 30 microns in size. It is most preferred that the water absorbent polymer particles are reduced to a fine powder preferably less than about 5 microns in size. These particles show aqueous absorbance capability in excess of 35 times their weight.

These water absorbing polymer particles swell when they absorb aqueous fluids. The particles maintain their approximate shapes and geometry but the dimensions thereof are greatly enlarged.

In preparing the articles of this invention, the water absorbing polymers may also be mixed with other particulate material which is insoluble in water and organic liquids which are capable of absorbing or adsorbing liquids. One example of other particulate matter is naturally occurring cellulose materials, such as saw dust, crushed corncobs, cotton linters, wood pulp, and the like. Another type of particulate matter useful in this invention is silica gel which can absorb fluids. Other useful absorbants are molecular-sieve zeolites, activated alumina and calcium sulfate, also known by the tradename Drierite.

Ion-exchange resins can also be used as another particulate material in combination with the water absorbing polymers of this invention. Particularly useful ion-exchange resins are the strong acid, cation exchange resins.

Other particulates which can be mixed with the water absorbing polymers for use in this invention are clay minerals, such as kaolin, montmorillonite, illite, vermiculite, glauconite, attapulgite and the like. These clay minerals are mixtures of metal oxides, e.g., aluminum oxide, magnesium oxide, potassium oxide, and silicon oxide, and generally exist in the amorphous state.

Once the water absorbent polymer is prepared, and combined with other particulate material, if appropriate, it is blended with a foamed latex material. Any conventional latex can be used in the preparation of the water absorbent polymer latex foam. For example the latex can be selected from the group consisting of acrylic, styrene-butadiene rubber, polyethylene, vinyl acetate, vinyl acetate/acrylic copolymers, polyvinyl chloride copolymers, nitriles, vinyl acetate homopolymers and styrene acrylic polymers, with acrylic or styrene-butadiene rubber latex the preferred latexes.

The preferred latex foam has a low water and high air content. In a preferred embodiment the percentage of water in the latex foam is less than about 60 percent.

Prior to foaming there can be added to the latex certain foaming agents to enhance the foaming tendency of the latex or to add crosslinking or other specific traits to the foam structure. Any conventional latex foaming agent or crosslinking agent can be used such as ammonium stearate, phosphate esters, ethozylated alcohols, azodicarbonamide, sodium laurel sulfate, sulfosuccinamates and mono-ester sulfosuccinates. Preferable latex foaming agents include sodium laural sulfate and sulfosuccinamates.

Prior to foaming of the foamable latex polymer, additional products may also be added to the foamable latex such as surfactants, fillers or non-woven fibers to further enhance the latex foam's properties. For example, in a preferred embodiment to assist in surface absorption, surfactants such as Pluronic-type surfactants may be added prior to the foaming operation. These products will enhance the capability of the latex foams in their absorbance by increasing the rate at which the water passes through the surface of the foam.

The latex material is foamed by any conventional foaming procedures and preferably is foamed by mechanical means using commercially available equipment manufactured by companies such as Oakes, Latex Equipment Sales and Services, XKG (Reddy, Pennsylvania) or Gaston County Sales and Services Corporation (Stanley, North Carolina).

The thickness of the latex foam can be any conventional thickness used in the casting of latex foams. However, in a preferred embodiment the thickness of the foam should be less than about 100 mls. By limiting the thickness of the foam to less than 100 mls, the latex foam will maintain its high water absorbency. When the thickness of the latex foam exceeds about 100 mls, the water absorbent capabilities of the foam may be reduced or the time of absorption may be increased.

After the latex material is foamed, the water absorbing polymer materials are blended with the latex foam. Any conventional method of blending known in the industry can be used for the blending of the water absorbent polymer with the latex foam. For example, the water absorbent polymer can be mechanically blended into the foam. In a preferred embodiment, the water absorbent polymer particulates are sprayed into the latex foam which has been cast onto a non-woven substrate. To effect the spraying of the water absorbent particles, the particles are suspended in the spraying medium, such as air, nitrogen or other gaseous environment, and then under pressure transported to a conventional spray nozzle. The water absorbent polymer particulates are then sprayed into the latex foam. The water absorbent particulates are anchored to the foam by the spraying process by penetrating the surface of the foam and becoming embedded in the foam structure, which distributes the water absorbent particulates evenly throughout the structure of the latex foam.

When mixing the water absorbent polymer with the foamed latex polymer, the percentage of the water absorbent polymer in relation to the foamed latex polymer may vary depending upon the degree of fluid absorption that is desired. Obviously the greater the percentage of water absorbent polymer within the latex foam, the greater the absorbent capabilities of the latex foam. However, when the percentage of the water absorbent polymer is too high, i.e. greater than about 75 percent, the structure of the latex foam begins to fall apart. Thus, in a preferred embodiment the percentage of water absorbent polymer within the water absorbent polymer latex foam should be from about 5 to about 45 percent and preferably from about 5 to about 25 percent of the overall structure.

In prior art water absorbent composites, the water absorbent particulates are generally distributed through a fibrous web with no chemical or physical means for attachment. This technique generated areas in a material which did not contain water absorbent materials, thus reducing the absorbency of the overall product. The instant procedure for producing water absorbent latex foams provides evenly distributed cellular residence for the water absorbent polymer particulates within the foam. In addition, the method of the instant invention allows a one-step continuous process for combining a latex foam with a water absorbent polymer particulate.

Following blending of the water absorbent polymer in the latex foam, the latex foam is dried in a conventional drying oven, preferably a hot air oven, with temperatures less than 200° C. until sufficient water has been driven off, i.e. for a period of about 15 seconds to 2 minutes depending on the temperature of the oven and the thickness of the foam material.

The latex containing the water absorbent polymer may be used alone or it may be secured to a non-woven substrate. Any conventional non-woven substrate can be used which will adhere or stay in contact with the latex foam. The preferred substrate onto which is cast the latex foam material is a flexible fabric which is permeable to liquid and can be bound easily to the latex foam material. The fabric can be made of any of the well known textile materials such as cotton, wool, rayon, acetate, acrylic, propylene, copolypropylene, polyester, nylon etc. with the preferred materials including polyesters, polypropylenes and nylons. The fabric can be woven or knitted, though non-woven materials such as those made by the chemical and mechanical bonding of dry laid webs, by wet processing using modified paper making techniques or spun bonding techniques are preferred. Of the non-woven materials, spun bonded fabrics are more preferable. In addition, the material of this layer can be produced from combinations of porous materials such as the combination of polyesters and cotton. This material exhibits good wicking qualities to transfer fluid through the material to the latex foam layer.

The latex foam with water absorbent polymer blended in their structure shows significant water absorbance depending on the thickness of the latex foam and the percentage of water absorbent polymer contained within the structure. With about 5 percent water absorbent polymer within the latex foam structure, the distilled water absorbance of the material is at least about 35 times the weight of the water absorbent polymer and at least about 12 times the weight of the water absorbent polymer in a one percent saline solution. When percentages of the water absorbent polymer in the latex foam approach 25 percent the absorption of distilled water increases to about 65 times the weight of the water absorbent polymer and up to about 14 times the weight in a one percent saline solution.

The following examples are given as specific illustration of the invention. All parts and percentages are by weight unless otherwise stated. It is understood however that the invention is not limited to specific details set forth in the examples.

EXAMPLE

A styrene-butadiene rubber (SBR) latex foam was cast on a wet-lay non-woven substrate. The SBR latex chosen was Unocal #83026, a hydrophilic SBR latex. Using a conventional stirring mechanism, 200 grams of SBR latex was foamed until the ratio of air to SBR latex was about 7:1. The SBR latex was agitated for about 3 to 4 minutes.

The substrate used to support the foam was a wet lay web comprised of 80 percent polyester and 20 percent wood pulp. Following the drying of this wet-lay web, the foamed SBR latex was spread while still wet on the substrate. Three different thicknesses of the SBR latex were prepared, respectively 20 mls, 80 mls and 40 ml. After the SBR latex was spread and the thickness was set, the water absorbent polymer was sprayed by a Nordson Air Fluidized Powder Spray apparatus into the SBR latex. The water absorbent material was a graft copolymer of about 91 percent acrylic acid and 9 percent oxidized starch crosslinked with 0.1 percent N,N'-methylene-bis-acrylamide made by the process described in U.S. Pat. No. 4,076,663. The water absorbent material comprised respectively 5 to 10 percent, 15 to 20 percent and 20 to 25 percent of the SBR latex mixture. The particulate size of the water absorbent material was generally less than about 30 microns.

After the water absorbent polymer was sprayed on to the SBR latex foam, the material was dried in an oven at 250° F. for approximately 15 to 20 seconds to 5 minutes. After the drying of the SBR latex material, tests were run on the foam to determine its absorbency in both distilled water and a 1 percent saline solution. Results of these test are shown on Table I.

TABLE I

| WATER ABSORBENT SBR LATEX FOAM | | | |
|---|---|---|---|
| Water Absorbant polymer percentage | 5–10 | 15–20 | 20–25 |
| THICKNESS, mls. | 20 | 80 | 40 |
| STATIC LIQUID ABSORPTION DISTILLED WATER | | | |
| % by weight | 3500 | 4500 | 6500 |
| 1% SALINE SOLUTION | | | |
| % by weight | 1200 | 1000 | 1400 |

As is apparent from these result, latex foams containing water absorbent polymers which absorb a large amount of water in relation to the weight of the foam can be produced. Latex foams of this type can be prepared using various types of substrates, various amounts of the water absorbent polymer and having different thicknesses. These foams will have great utility because of their high degree of water absorbance in comparison with conventional latex foams.

What is Claimed:

1. A water absorbent latex polymer foam prepared by the process of:
   a. preparing a foamable latex polymer material;
   b. foaming said latex polymer material;

c. blending a water absorbent polymer with the latex foam material; and d. drying the latex foam material containing the water absorbent polymer within its structure to form a water absorbent latex polymer foam.

2. A water absorbent latex polymer foam prepared by the process of:

a. preparing a styrene-butadiene rubber latex polymer material;
   b. foaming said styrene-butadiene rubber polymer material;
   c. blending a water absorbent polymer particulate with the styrene-butadiene rubber latex foam; and
   d. drying the styrene-butadiene rubber foam material containing within its structure the water absorbent polymer to form a styrene-butadiene rubber latex foam with water absorbent polymer within its structure.

3. The water absorbent latex polymer foam as in any of claims 1 or 2 wherein the water absorbent polymer comprises about 5 to 45 percent of the structure of the foam material.

4. The water absorbent latex polymer foam as in any of claims 1 or 2 wherein the water absorbent polymer comprises 5 to 25 percent of the structure of the foam material.

5. A water absorbent latex polymer foam product prepared by the process of:

a. preparing a foamable latex polymer material;
   b. foaming said foamable latex polymer material;
   c. blending a water absorbent polymer particulate with the latex foam material;
   d. drying the latex foam material containing water absorbent polymer particulates within its structure to form a water absorbent latex foam containing the water absorbent polymer particulates within its structure; and
   e. securing the water absorbent latex foam containing the water absorbent polymer particulates within its structure to a substrate to form a water absorbent latex polymer foam secured to a substrate.

6. A water absorbent polymer foam product prepared by the process of:

a. preparing a styrene-butadiene rubber latex polymer material;
   b. foaming said styrene-butadiene rubber latex polymer material;
   c. blending a water absorbent polymer particulate with the styrene-butadiene rubber latex foam;
   d. drying the styrene-butadiene rubber latex foam containing water absorbent polymer particulates within its structure to form a water absorbent styrene-butadiene rubber latex foam containing the water absorbent polymer particulate within its structure; and
   e. securing the styrene-butadiene rubber latex polymer foam containing the water absorbent polymer particulate to a non-woven substrate to form a water absorbent styrene-butadiene rubber latex polymer foam secured to a substrate.

7. The water absorbent polymer foam material as in any of claims 1, 2, 5 or 6 wherein the size of the water absorbent particulate is from about 0.5 micron to about 1,000 microns.

8. The water absorbent polymer foam material as in any of claims 1, 2, 5 or 6 wherein the size of the water absorbent particulate is less than about 20 microns.

9. A water absorbent latex foam material prepared by blending water absorbent polymer particulates with a foamable latex, wherein the water absorbed polymer particulates comprise at least about 5 percent of the latex foam material, and wherein the material is capable of absorbing at least about 35 times the weight of the water absorbent polymer particulates in water and about 12 times the weight of the water absorbent polymer particulates in a one percent saline solution.

10. The water absorbent latex polymer foam product as in any of claims 5 or 6 wherein the substrate is a non-woven fabric prepared by spin bonding.

11. The water absorbent latex polymer foam as in any of claims 1, 5 or 9 wherein the latex is selected from the group consisting of acrylic latex, styrene-butadiene rubber latex, polyethylene latex, vinyl acetate latex, vinyl acetate/acrylic copolymer latex, polyvinyl chloride latex, nitrile latex, vinyl acetate latex and styrene acrylic latex.

12. The water absorbent latex polymer foam as in any of claims 1, 2, 5 or 6 wherein there is additionally added to the foamable latex polymer, an absorbent material selected from the group consisting of naturally accruing cellulose materials, silica gel, a clay mineral, metal oxides and cellular organic polymers.

* * * * *